United States Patent [19]

Black

[11] 4,171,358
[45] Oct. 16, 1979

[54] NOVEL CONTRACEPTIVE METHOD

[75] Inventor: Larry J. Black, Indianapolis, Ind.

[73] Assignee: Eli Lilly and Company, Indianapolis, Ind.

[21] Appl. No.: 677,951

[22] Filed: Apr. 19, 1976

Related U.S. Application Data

[63] Continuation-in-part of Ser. No. 462,458, Apr. 19, 1974, abandoned.

[51] Int. Cl.$^2$ .............................................. A61K 31/56
[52] U.S. Cl. .................................................. 424/243
[58] Field of Search ........................................ 424/243

[56] References Cited

U.S. PATENT DOCUMENTS

| | | | |
|---|---|---|---|
| 3,758,687 | 9/1973 | Ufer et al. | 424/243 |
| 3,822,355 | 7/1974 | Kincl | 424/243 |
| 3,828,106 | 8/1974 | Rudel | 424/239 |

OTHER PUBLICATIONS

Chemical Abstracts (1972), vol. 77, Pars. 10849.

*Primary Examiner*—Elbert L. Roberts
*Attorney, Agent, or Firm*—James L. Rowe; Everet F. Smith

[57] ABSTRACT

Progestational agents administered daily to female mammals during the follicular phase only of the cycle prevents uterine development associated with implantation in the luteal phase, thereby preventing conception.

5 Claims, No Drawings

NOVEL CONTRACEPTIVE METHOD

CROSS-REFERENCE

This application is a continuation-in-part of my copending application Ser. No. 462,458 filed Apr. 19, 1974 now abandoned.

BACKGROUND OF THE INVENTION

The commonly used method of oral contraception in human females consists of a combination of estrogen and progestin (progestational agent) administered daily for 21 days. Menstruation occurs about 3 to 5 days after withdrawal and administration is reinitiated after 8 days, thereby beginning a new cycle. Inhibition of ovulation by the progestin is believed to be the primary effect of this contraceptive method. Rudel, et al., *Fertility and Sterility*, 16, 158–169, (1965) pointed out, however, that progestins, in addition to their antiovulatory action, have other antifertility effects including the production of a state of maturation of the endometrium which is out of phase with ovulation, accompanied by changes in the cervical mucus, these changes being incompatible with vital and motile spermatozoa. The authors suggested that, in an oral contraceptive agent comprising a combination of progestin and estrogen, these other effects (in addition to inhibiting ovulation) of progestins may be lost in the presence of added estrogen. Martinez-manaoutou, et al., ibid, 17, 49–57 (1966) has also suggested that a low dose of a progestin, specifically chlormadinone acetate—a progestin without estrogenic activity—prevented conception when administered continuously at the rate of 0.5 mg. per day to human females during an entire ovulatory cycle. It was determined that ovulation probably occurred in 60 percent of the patients. Only one pregnancy occurred in 416 patients and 1600 menstrual cycles. From these observations, the authors advocated the continuous administration of minimal doses of a progestin as a contraceptive method in human females. The same laboratory reported, ibid, 17, 57–62 (1967) that chlormadinone acetate when administered to human females at a dosage of less than 500 mcg. daily demonstrated anti-estrogenic influence on the cervical mucus without suppression of endometrial development. The contraceptive effectiveness of the administered progestational agent appeared to parallel closely the changes in the cervical mucus. The same research group repeated in ibid, 18, 219–221 (1967) their previous findings that a progestin given at dose levels which do not inhibit ovulation is able to create a state of hormonal imbalance as evidenced by a suppressed endometrium and/or a thickened, scanty cervical mucus. The daily low level administration of a progestin throughout the menstrual cycle was the contraceptive method advocated by the authors for human population control on a large scale, and they specifically advocated the employment of an implanted pellet which would meter out the progestin for a month or six weeks. The authors also advocated the administration of estrogens after ovulation has occurred in the hope that such administration would create another hormonal imbalance hostile to conception and thus promote contraception. In summary, this research group has found that the low daily dosage of chlormadinone acetate (0.5 mg. daily), a progestin without estrogenic activity, throughout the menstrual cycle afforded a contraceptive method with an efficacy comparable to the well-known marketed estrogen-progestin combinations.

Ufer, et al., U.S. Pat. No. 3,758,687 issued Sept. 11, 1973 covers the administration to a female human at some point during the interval from the 5th to the 8th day of the menstrual cycle of a depot formulation of a progestin so as to prevent conception during the remainder of the cycle and possibly for 2-3 cycles. The depot formulation pays out the progestin continuously so that there is a measureable amount present for at least one cycle and perhaps longer. Kincl, U.S. Pat. No. 3,822,355 discloses the administration of a progestational agent only during the luteal phase of the menstrual cycle. Schmitt, et al. *Chemical Abstracts*, 77, 10849 (1972) disclose the continuous administration of a gestagen, specifically chlormadinone, at low levels (minipills). The regimen employed was a failure since half of the thirty-five women in the test group showed bleeding disturbances. Rudel, U.S. Pat. No. 3,828,106, discloses an oral pharmaceutical form for administering steroid hormones.

A relationship between the progestational state of the uterus and implantation was reported originally by Corner and Allen, *Am. J. Physiol.*, 86, 74 (1928), 88, 340 (1929). The necessity of pretreatment with the follicular hormone (estrogen) for optimal response to the luteal hormone (progesterone) was later observed by many others including Allen, *Am. J. Physiol.*, 92, 612 (1930) and Hisaw and Leonard, *Am. J. Physiol.*, 92, 574 (1930). The phenomenon of sequential influence of ovarian steroids is now widely accepted by research workers studying mammalian reproductive cycles.

Estrogen priming is apparently not indispensable for a response to a progestin, but the priming lowers the threshold for progestational responses including progestational proliferation, increased carbonic anhydrase, Pincus et al. *Endocr.*, 61, 528 (1957), and synthesis of DNA and mitosis, Lee and Dukelow, *J. Reprod. Fert.*, 31 473 (1972). Rudel, et al., *J. Reprod. Fert.*, 8, 305 (1964), observed that the progestational response to chlormadinone acetate, a typical progestin, in humans is directly related to the degree of estrogen stimulation of the endometrium at the time treatment is started.

SUMMARY OF THE INVENTION

This invention provides a novel contraceptive method comprising the daily administration of a progestin to a female mammal only during the proliferative or follicular phase of the menstrual cycle with no hormone being administered during the luteal phase. Customarily, according to my novel contraceptive method, the progestin is first administered to the cycling female mammal on the day following the cessation of bleeding and administration of the progestin continues on a daily basis during the first half, or the proliferative phase of the cycle. Administration of the progestin is then discontinued and no hormone, either estrogen or progestin is administered during the second half, or luteal phase, of the cycle. With an average human female, for example, this method of contraception would involve self administration by the cycling female of a progestational agent on a daily basis for the period beginning on day 6 and continuing through day 16 of the cycle only with no hormone or, alternatively, with a placebo being administered and then stopping. The progestin dose level employed is that amount of a progestin equivalent to 300-500 mcg. of chlormadinone acetate per day for a human female or at the rate of about 5-8 mcg./kg./day of female mammalian body weight for each day of the follicular phase. As specified, the amount of progestational agent administered is that amount which will give a progestational effect equivalent to that given by the above dose levels of chlormadinone acetate. Other progestational agents which can be employed in my novel contraceptive process at dose levels giving an equivalent progestational effect to that of 5–8 mcg. of chlormadinone acetate/kg./day include progesterone (pregn-4-ene-3,20-dione), norprogesterone (17β-acetylestra-4-en-3-one), provera (17-hydroxy-6α-methylpregn-4-ene-3,20-dione acetate), norethindrone (17α-ethynyl-17β-hydroyestr-4-en-3-one), norgestrel (dl-13β-ethyl-17α-ethynyl-17β-hydroxygon-4-en-3-one), norethynodrel (17α-ethynylestr-4-en-3β,17-diol diacetate), 16α-chloroprogesterone (16α-chloropregn-4-ene-3,20-dione), 6α-chloro-16α-methylprogesterone (6α-chloro-16α-methylpregn-4-ene-3,20-dione), chlormadinone (6-chloro pregna-4,6-dien-17α-ol-3,20-dione), norethandrone (17α-ethyl-19-nortestosterone), Δ4,9-progesterone [19-nor-4,9(10)-pregnadiene-3,20-dione] and the like. Dosages of these other progestational agents which are equivalent to the above range of doses set forth for chlormadinone acetate depend upon both the nature of the compound and the route of administration. For example, norethandrolone is five times more active than progesterone subcutaneously but fifty times more active orally. Chlormadinone acetate is fifty times more active than norethandrolone and five hundred times more active than norethindrone by injection and fifty times more active than either orally. Thus, a daily oral intake of chlormadinone acetate of from 300–500 mcg. per female would be equivalent to 15–25 mg. per female per day of norethindrone. Similar equivalencies of other agents as progestins to chlormadinone acetate can be determined experimentally, and their dosage levels in my novel process can in turn be determined from these data.

Unlike the regimen proposed by Ufer, U.S. Pat. No. 3,758,687, wherein there is a single administration of a depot formulation which continuously pays out the progestin into the blood stream for a period equivalent to at least as long as one cycle, applicant utilizes a daily dose regimen during the follicular phase only so as to limit the progestational influence to the pre-ovulatory phase.

While all progestational agents will prevent conception in female mammals when administered at the rates set forth above, a preferred group will be those classified as Type B progestational agents according to the classification of Black and Kraay, *J. Steroid. Biochem.*, 4, 467 (1973). In general, these compounds will be structurally related to the natural hormone, progesterone, which has a β-acetyl group at $C_{17}$. While an hydroxy or acetoxyl group may also be present at $C_{17}$ in these compounds, these oxygen functions will invariably have the α-orientation since it is apparently the orientation of the 17-hydroxyl which decrees whether a given progestin will be Type A or Type B according to the criterion of Black and Kraay (loc. cit.).

Suppression of uterine responsiveness to progesterone is apparently achieved through interference with the sensitizing effects of estrogen. Administration of an estrogenic agent is less effective due to its estrogenic contribution during the estrogen priming phase.

The ability of progestational agents to affect the progestational response by inhibiting fertility without inhibiting ovulation is illustrated by the following experiment in which immature Dutch Belted rabbits were primed with daily injections of 0.5 mcg. of estradiol for six days followed by doses of 100 mcg. of progesterone for five days. The group of progestins under test were first administered at various dose levels only during the estrogen priming phase to determine their effect upon the uterine response, which was measured by sacrificing the rabbit, taking a 6 micron section of each uterus, using both horns of individual animals, mounting the tissue and then staining the tissue with hematoxylin-eosin. The progestational responses were graded on a scale of 0–4 according to the method of McPhail, *J. Physiol.*, 83, 145 (1934). The mean response in 64 animals receiving only estrogen in the estrogen-priming phase was 3.3. Table 1 below gives the results of these determinations. In the table, column 1 gives the name of the progestational agent administered during the estrogen-priming phase, column 2, the number of animals used, column 3, the dose of the progestational agent used for 6 days against the standard dose of estrogen, specifically estradiol, column 4, the uterine response graded on scale of from 0 to 4 as previously set forth, and column 5, the standard error.

TABLE 1

The Effect of Administration of Progestins in the Estrogen Priming Phase

| Progestin | No. of Animals | Dose/d × 6 vs $E^2$ | x̄ Uterine Response | S.E. |
|---|---|---|---|---|
| None | 64 | — | 3.3 | 0.1 |
| Progesterone | 6 | 1 mg | 0.1 | 0.1 |
| Progesterone | 6 | 300 μg | 0.4 | 0.1 |
| Progesterone | 6 | 100 μg | 1.3 | 0.2 |
| Progesterone | 6 | 30 μg | 1.6 | 0.2 |
| Norgestrel | 6 | 100 μg | 0.5 | 0.1 |
| Norgestrel | 6 | 30 μg | 0.4 | 0.1 |
| Norgestrel | 6 | 10 μg | 2.2 | 0.2 |
| Provera | 6 | 300 μg | 0.3 | 0.1 |
| Provera | 6 | 100 μg | 0.2 | 0.1 |
| Provera | 6 | 30 μg | 0.1 | 0.1 |
| Norprogesterone | 6 | 300 μg | 0 | — |
| Norprogesterone | 6 | 100 μg | 0.2 | 0.1 |
| Norprogesterone | 6 | 30 μg | 0.6 | 0.1 |
| 6α-Chloro-16α-methyl progesterone | 6 | 1 mg | 0.4 | 0.1 |
| | 5 | 300 μg | 0.4 | 0.1 |
| | 2 | 100 μg | 3.5 | 0.3 |
| 16α-Chloro-progesterone | 6 | 3 mg | 0.4 | 0.1 |
| | 6 | 1 mg | 1.8 | 0.2 |
| | 6 | 300 μg | 2.3 | 0.3 |
| Nortestosterone | 6 | 1 mg | 2.4 | 0.3 |

TABLE 1-continued

| The Effect of Administration of Progestins in the Estrogen Priming Phase | | | | |
|---|---|---|---|---|
| Progestin | No. of Animals | Dose/d × 6 vs $E^2$ | x̄ Uterine Response | S.E. |
| Nortestosterone | 6 | 300 μg | 2.7 | 0.1 |
| Nortestosterone | 6 | 100 μg | 3.3 | 0.1 |
| Norethynodrel | 6 | 1 mg | 1.7 | 0.2 |
| Norethynodrel | 6 | 300 μg | 2.8 | 0.2 |
| Norethynodrel | 6 | 100 μg | 3.2 | 0.2 |
| Norethindrone | 6 | 300 μg | 0.2 | 0.1 |
| Norethindrone | 6 | 100 μg | 1.8 | 0.2 |
| Norethindrone | 6 | 30 μg | 1.8 | 0.1 |
| Ethynodiol Diacetate | 6 | 1 mg | 0.7 | 0.1 |
| Ethynodiol Diacetate | 6 | 300 μg | 1.4 | 0.2 |
| Ethynodiol Diacetate | 5 | 100 μg | 1.5 | 0.2 |
| Chloromadinone Acetate | 12 | 100 μg | 0.3 | 0.1 |
| Chloromadinone Acetate | 6 | 30 μg | 0.2 | 0.1 |
| Chloromadinone Acetate | 11 | 10 μg | 0.2 | 0.1 |
| Chloromadinone Acetate | 9 | 3 μg | 1.8 | 0.2 |
| Δ4,9-Progesterone | 3 | 1 mg | 0 | — |
| Δ4,9-Progesterone | 3 | 300 μg | 0.2 | 0.1 |
| Δ4,9-Progesterone | 3 | 100 μg | 0 | — |
| Δ4,9-Progesterone | 3 | 30 μg | 0.5 | 0.2 |

In order to demonstrate that continued administration of progestins through both the follicular and luteal phases of the menstrual cycle is deleterious to the uterine effects of administered progestin, a modification of the above experiment was carried out in which the progestin was administered during both the estrogen and progesterone administration phases of the cycle. Table 2 which follows gives the result of these determinations in which the uterine response was measured as before. In the table, column 1 gives the name of the progestin administered, column 2, the number of animals used, column 3, the dosage of progestin administered during the estrogen priming phase, column 4, the dosage of progestin administered during the progesterone injection phase, and columns 5 and 6, the uterine response measured as before, and the standard error.

TABLE 2

| The Effect of Administration of Progestins in the Estrogen Priming and Progestin Phases | | | | | |
|---|---|---|---|---|---|
| Progestin | No. of Animals | Dose/d × 6 vs $E^2$ | Dose/d × 5 vs Prog. | x̄ Uterine Response | S.E. |
| None | 64 | — | — | 3.3 | 0.1 |
| Progesterone | 6 | 300 μg | 300 g | 2.7 | 0.1 |
| Norgestrel | 6 | 100 μg | 100 g | 2.5 | 0.2 |
| Provera | 6 | 100 μg | 100 g | 2.7 | 0.1 |
| Norprogesterone | 6 | 300 μg | 300 g | 1.8 | 0.3 |
| 6α-Chloro-16α- | — | — | — | 3.5 | 0.3 |
| methyl progesterone | 5 | 300 μg | 300 g | 3.0 | 0.2 |
| 16α-Chloro progesterone | 6 | 3 mg | 3 mg | 3.5 | 0.3 |
| Nortestosterone | 6 | 1 mg | 1 mg | 2.3 | 0.3 |
| Norethynodrel | 5 | 1 mg | 1 mg | 2.1 | 0.3 |
| Norethindrone | 6 | 300 μg | 300 g | 1.3 | 0.3 |
| Ethynodiol Diacetate | 6 | 1 mg | 1 mg | 1.6 | 0.4 |
| Chloromadinone Acetate | 12 | 100 μg | 100 g | 2.4 | 0.2 |

As can be seen from Table 2, the continuation of administration of the progestin during the progestational (luteal) phase of the cycle tends to eliminate the suppression of uterine response seen when the progestin is administered only during the estrogen (follicular) phase of the cycle. In most instances in fact, the uterine response is so close to the uterine response of the control animals (3.3) that a progestin administered under these conditions does not sufficiently suppress the uterine state to act reliably as an antifertility or contraceptive agent and the possibility of pregnancy would be encountered.

Progestins useful in the novel contraceptive process of this invention can be administered to female mammals either orally or parenterally. The orally active progestins, in general those compounds which possess a 17α-acetoxy group, are conveniently administered in the form of tablets or capsules. For administration in these pharmaceutical forms, the compound is mixed with a pharmaceutically-acceptable excipient and the mixture either loaded into telescoping gelatin capsules or binders; lubricants and the like are also added and the new mixture pressed into tablets. Each tablet or capsule contains a dose of the progestin sufficient to prevent conception when taken daily during the follicular phase. With those progestins which are not orally active, as for example progesterone itself, the compound is preferably administered intramuscularly or intraperitoneally to the female mammal. This parenteral mode of administration is preferred for those mammals who are unable to take oral medication. In carrying out the novel processes of this invention with human females, however, the oral mode of administration is preferred. For such purposes, the medication is placed in a dispenser containing a calendar on its face and 21 or 28 pill slots. On a 21-day regimen, the first 10 slots are filled with progestin-containing tablets and the last 11 slots are filled with placebo tablets. With the 28-day dispenser, the first 10 slots are filled with the progestin-containing tablets and the last 18 slots are filled with placebo tablets. In either case, the human female takes pill number 1 on day 1 which is the first day after the cessation of bleeding from her last menstrual period and continues till the dispenser is empty, starting with a new dispenser on day 1 of her next cycle. An alternative mode of administration would involve a dispenser with the first seven slots filled with placebo tablets, then 10 slots filled with medication followed by 11 slots again filled with placebo tablets. With this dispenser, the human female would take the first placebo tablet on the first day of menstruation.

I claim:

1. A contraceptive method comprising the daily administration of a progestin to a female mammal during the follicular phase of the menstrual cycle at a dose insufficient to suppress ovulation in a majority of female mammals and then administering no hormone during the luteal phase of the menstrual cycle.

2. A process according to claim 1 in which the amount of progestin administered to a human female is equivalent to an oral dosage of 300 to 500 mcg. of chlormadinone acetate per day.

3. A process according to claim 1 in which the dosage of progestin administered is equivalent to an oral dosage of chlormadinone acetate of from 5 to 8 mcg./kg. of female mammalian body weight per day.

4. A contraceptive method for female humans comprising daily administration of a progestin to a human female starting day 6 of the menstrual cycle and continuing through day 16, day 1 of the menstrual cycle being the day when the period commences, followed by an absence of hormone administered during days 17–28 of the menstrual cycle.

5. A process according to claim 4 in which amount of progestin equivalent to a daily oral dose of 300 to 500 mg. of chlormadinone acetate is administered per day to a human female during the 11-day period.

* * * * *